United States Patent [19]

Foshee

[11] Patent Number: 5,257,975
[45] Date of Patent: Nov. 2, 1993

[54] CANNULA RETENTION DEVICE

[75] Inventor: David L. Foshee, Cary, N.C.

[73] Assignee: Edward Weck Incorporated, Research Triangle Park, N.C.

[21] Appl. No.: 930,768

[22] Filed: Aug. 14, 1992

[51] Int. Cl.$^5$ .............................................. A61M 5/32
[52] U.S. Cl. ...................................... 604/105; 604/175
[58] Field of Search ................ 604/175, 174, 104, 105, 604/96

[56] References Cited

U.S. PATENT DOCUMENTS

| | | |
|---|---|---|
| 1,621,159 | 3/1927 | Evans . |
| 3,039,468 | 6/1962 | Price . |
| 3,108,595 | 10/1963 | Overment .................. 604/105 |
| 3,261,357 | 7/1966 | Roberts et al. . |
| 3,713,447 | 1/1973 | Adair . |
| 3,717,151 | 2/1973 | Collett . |
| 3,774,596 | 11/1973 | Cook . |
| 3,882,852 | 5/1975 | Sinnreich . |
| 3,915,171 | 10/1975 | Shermeta ..................... 604/104 |
| 3,938,530 | 2/1976 | Santomieri .................. 604/105 |
| 4,043,338 | 8/1977 | Homm et al. ................ 604/105 |
| 4,198,981 | 4/1980 | Sinnreich . |
| 4,240,433 | 12/1990 | Bordow . |
| 4,250,873 | 2/1981 | Bonnet . |
| 4,608,965 | 9/1986 | Anspach et al. . |
| 4,699,611 | 10/1987 | Bowden . |
| 4,861,334 | 8/1989 | Nawaz . |
| 4,921,484 | 5/1990 | Hillstead ..................... 604/104 |
| 4,995,868 | 2/1991 | Brazier . |
| 5,053,009 | 10/1991 | Herzberg . |
| 5,112,321 | 5/1992 | Hiltebrandt . |
| 5,163,949 | 11/1992 | Bonutti . |

FOREIGN PATENT DOCUMENTS

| | | |
|---|---|---|
| 0368473 | 5/1990 | European Pat. Off. . |
| 0432363 | 6/1991 | European Pat. Off. . |
| 640126 | 12/1936 | Fed. Rep. of Germany . |
| 641240 | 1/1937 | Fed. Rep. of Germany . |
| 647326 | 7/1937 | Fed. Rep. of Germany . |
| 2238508 | 8/1972 | Fed. Rep. of Germany . |
| 4021153 | 1/1992 | Fed. Rep. of Germany . |
| 748666 | 7/1933 | France . |
| 11277 | of 1908 | United Kingdom . |
| 955490 | 4/1964 | United Kingdom ................ 604/105 |

OTHER PUBLICATIONS

The Gazayerli Endoscopic Retractor Model 1, M. M. Gazayerli, M.D., D.S., F.R.C.S.(C.).

Primary Examiner—Paul J. Hirsch
Attorney, Agent, or Firm—Rosenblatt & Associates

[57] ABSTRACT

The invention relates to a cannula with a fixation mechanism actuable to secure the cannula above and below the body wall in a single operation. The preferred embodiment involves spiral slit tubing in the form of a sleeve secured to the distal end of the cannula while mounted loosely over the cannula at the proximal end. A motion, such as twist and/or translation, is applied to the sleeve to make the spiral slit tubing expand to fixate the cannula.

23 Claims, 2 Drawing Sheets

CANNULA RETENTION DEVICE

FIELD OF THE INVENTION

This invention relates to medical instruments such as cannulas and ways to secure them to a body opening.

BACKGROUND OF THE INVENTION

In laparoscopic surgery, access to the surgical site is gained by small a incision in the body wall through which cannulas are passed. The cannula is essentially a tube equipped with a valve to prevent loss of gas which has been used to inflate the body cavity. Various instruments are inserted into the body cavity through the cannula. One or more cannulas can be used during a procedure, and sometimes as many as four or six can be used during a given procedure. During the procedure, the surgeon manipulates the instruments in the cannulas sometimes using more than one instrument at a time.

The action of the surgeon in manipulating the instruments causes frictional forces between the instrument and the cannula valve, which results in cannula movement responsive to movements of the instruments by the surgeon's hand. The potential exists for the cannula slipping out of the body wall which causes a loss of pneumoperitoneum. This situation creates difficulty of reinserting the cannula and delays the procedure.

In the past, cannulas have been attached to the body wall by separate mechanisms. One mechanism engages the underside of the body wall to prevent cannula pullout. The other mechanism is put in place outside the body wall to prevent the cannula from being pushed in. These separately actuable mechanisms for securing the cannula against pull out or push in present problems in reliability of engagement to the body wall and difficulty in obtaining the necessary fixation of the cannula to the body wall. Several prior designs have involved toggle bolt type operation, which has resulted in needless tissue trauma in the area inside the body wall, and a cumbersome procedure to engage the cannula.

In the past, various mechanisms have been used to secure placement of a variety medical devices. Some have employed a sliding sleeve technique which, upon longitudinal movement, causes a flexible member to expand outwardly adjacent the distal end of the instrument. Toward the proximal end, a flange or other mechanical means are employed so that the flexible member and the flange help to retain the instrument. Typical of such devices are U.S. Pat. No. 3,713,447; German Patent No. 2238508 (German equivalent of U.S. Pat. No. 3,713,447); German Patent No. 4021153A1 (mechanical linkage at distal end); European Patent No. 0432363A2; European Patent No. 0368473 and its U.S. equivalent, U.S. Pat. No. 4,995,868. Yet, other fixating mechanisms for insertable instruments into the body have featured a toggle-type mechanism at the distal end of the instrument to fixate it within the body wall. Typical of such devices are the Gazayerli Endoscopic Retractor Model 1 which has a toggle assembly at the distal end. Also, along this line, are German Patent No. 640126, which has alternative embodiments of a toggle arrangement that recedes into a sleeve, as well as a flexible member that can be expanded from the proximal end of the instrument. French Patent No. 748666 has pivoting members that flip up upon the shifting of a sleeve to retain the trocar to the inside of the body opening. Other toggle-type arrangements at the distal end are shown in British Patent No. 11277; U.S. Pat. Nos. 4,608,695; 3,261,357; and 3,039,468. Other devices employ longitudinal cutouts in a sleeve member making its distal end flexible when subjected to a compressive force. The radial expansion assists in positioning of the instrument. Typical of such devices are U.S. Pat. No. 5,053,009; 1,621,159; 4,258,073; and 4,699,611. German Patent Nos. 647326 and 641240 again illustrate flexible sleeves expanding radially-outwardly at the distal end of the instrument under a compressive force to assist in holding the position of the instrument. U.S. Pat. No. 3,717,151 has a plurality of fingers which are biased radially outwardly to prevent pullout of a flesh penetrating apparatus. U.S. Pat. No. 4,861,334 uses a balloon to hold the position of a gastronomy tube. Other patents illustrating the use of inflatable means to either assist in retaining the position of an instrument or for other purposes are U.S. Pat. Nos. 4,244,033 and 4,198,981.

What has been lacking in prior designs is a simple-to-use and simple-to-build reliable mechanism for fixating the cannula with respect to the body wall. Another feature which is desirable and not present in the prior designs is a simple to control fixating mechanism which is flexible and, therefore, sensitive to the surrounding tissue and the body wall, yet, at the same time, acting closely inside and outside the body wall to firmly and securely hold the cannula in the desired position as the procedure progresses. Those, and other, advantages of the invention will be described below.

SUMMARY OF THE INVENTION

The invention relates to a cannula with a fixation mechanism actuable to secure the cannula above and below the body wall in a single operation. The preferred embodiment involves spiral slit tubing in the form of a sleeve secured to the distal end of the cannula while mounted loosely over the cannula at the proximal end. A motion, such as twist and/or translation, is applied to the sleeve to make the spiral slit tubing expand to fixate the cannula.

DETAILED DESCRIPTION OF THE PREFERRED EMBODIMENT

Figure 2:
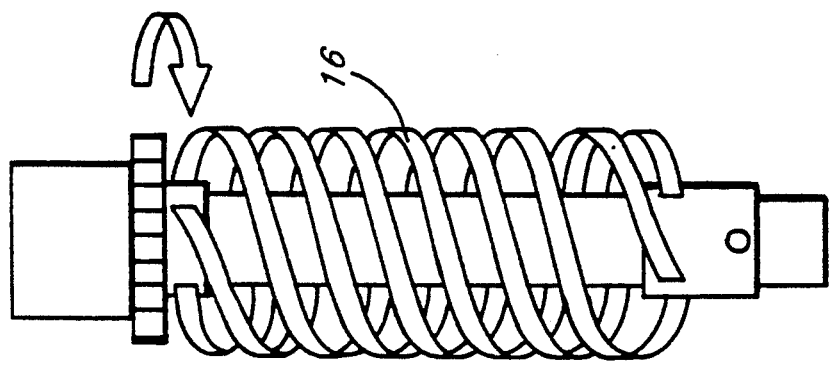
FIG. 2 shows the view of FIG. 1 with the spiral slit tubing in the expanded position.
Figure 1:
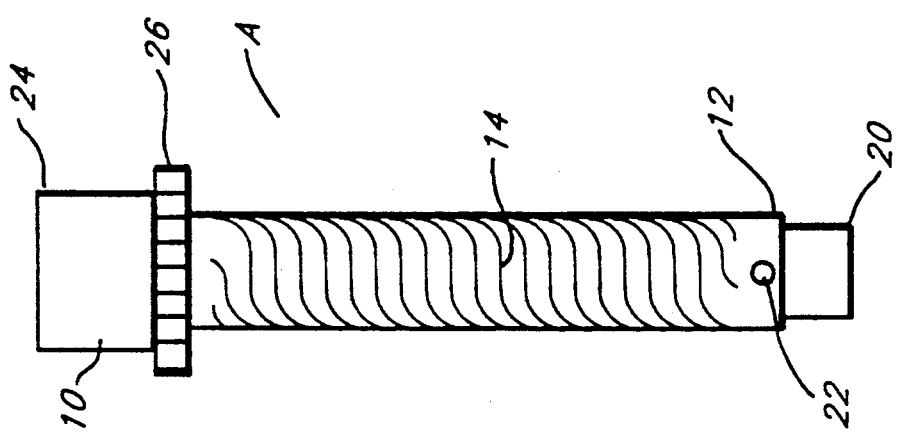
FIG. 1 shows the cannula with the spiral slit tubing in the contracted position.
Figure 6:
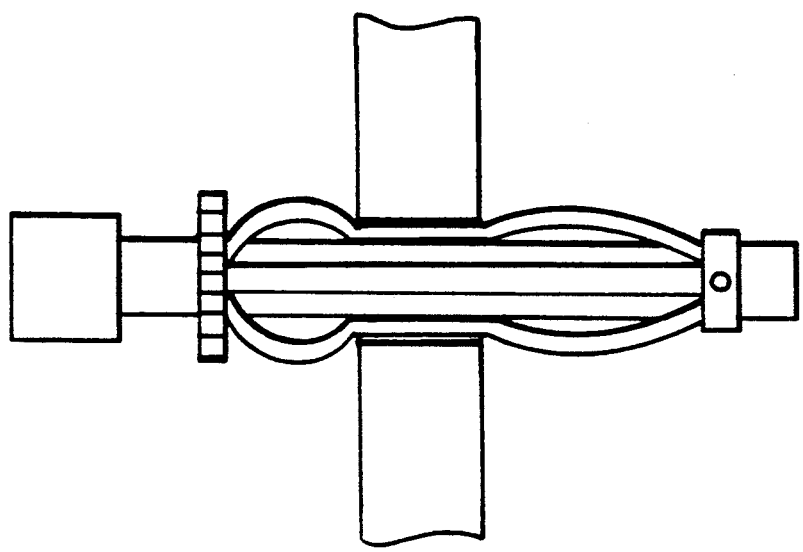
FIG. 6 is the view of FIG. 2 showing longitudinal strips expanded while the cannula is in place through an opening in the body wall.
Figure 5:
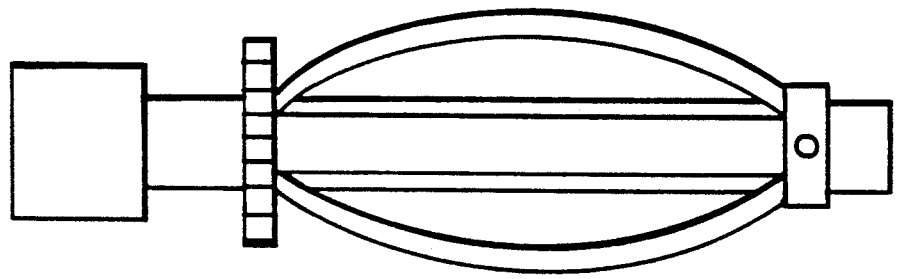
FIG. 5 shows the view of FIG. 1 with longitudinal strips in the expanded position.

The apparatus A is shown in FIG. 1. A cannula 10 is shown with sleeve 12 circumscribing cannula 10. Sleeve 12 has spiral slits 14. As better seen in FIG. 2, when the sleeve is expanded, a plurality of nested helixes 16 separate from the position illustrated in FIG. 1. As they separate, their diameter increases which is how the sleeve 12 fixates the cannula 10 to the body wall 18 (see FIG. 3). In the preferred embodiment, the sleeve 12 is fixed adjacent the distal end 20 of cannula 10. The manner of securing sleeve 12 to cannula 10 can take many forms, such as adhesive, an interference fit, or a clearance fit, or a fastener 22, as illustrated in FIG. 1. At its opposite end, sleeve 12 expands toward the proximal end 24. To facilitate operation, sleeve 12 has a knob 26, which can be gripped by the surgeon during the fixation of the cannula 10. Those skilled in the art will appreciate that as nested helixes 16 expand to the position shown in FIG. 2, the knob 26 can be twisted and/or translated closer to the distal end 20 of the cannula 10. It is necessary to fix the position of knob 26 once it is actuated to the position shown in FIG. 3. Fixation is required to ensure that the nested helixes 16 retain their expansion. This can be accomplished in a number of ways. There can be a slight dragging or clearance fit between the cannula 10 and the internal dimension of knob 26. This permits rotation and/or translation of knob 26 with the knob 26 retaining its position. Another way to accomplish the fixation of knob 26 is a thread form that is applied to cannula 10 with a mating thread on the inside of knob 26 whereupon clockwise rotation of knob 26 results in expansion of the nested helixes 16, as shown in FIG. 2. The sleeve 12 expands because it is fixed to the cannula adjacent distal end 20. The body of cannula 10 is retained by the surgeon while knob 26 is rotated to result in the radial expansion shown in FIGS. 2 and 3.

Figure 3:
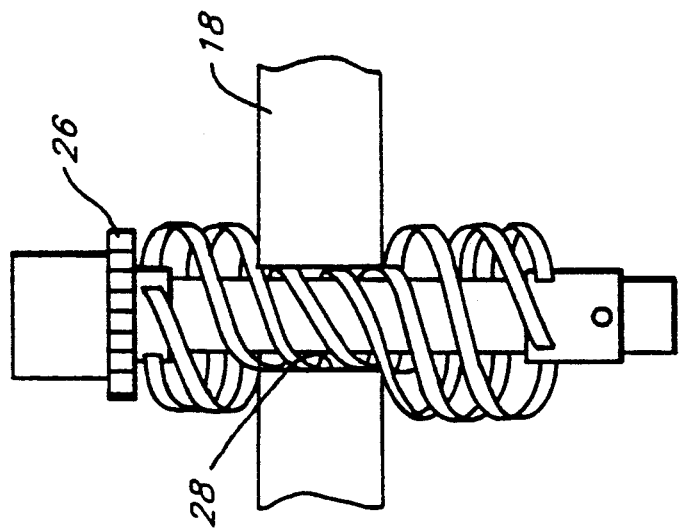
FIG. 3 is the view of FIG. 2 showing the spiral slit tubing expanded while the cannula is in place through an opening in the body wall.

The fixation of the cannula 10 is shown in FIG. 3. The cannula 10 is inserted through an opening 28 in the body wall 18 to the desired depth. Thereafter, the surgeon grabs the proximal end 24 of cannula 10 and rotates and/or translates knob 26. The rotation and/or translation results in the helixes 16 expanding above and below body wall 18 as shown in FIG. 3. Since the opening 28 is smaller and provides resistance to expansion of the nested helixes 16, such helixes 16 expand on either side of the opening 28 resulting in fixation of cannula 10 by virtue of knob 26 holding its relative position on cannula 10. Outside the body there is virtually no resistance to the expansion while inside the wall if there is low resistance from the surrounding tissue.

Those skilled in the art will appreciate other forms of execution of sleeve 12 can be employed without departing from the spirit of the invention. For example, sleeve 12 may have longitudinal as opposed to helical slits. In this embodiment, longitudinal depression of knob 26 while retaining cannula 10 will exhibit the same effect as shown in FIG. 3. The strips resulting from the slits will expand both and below opening 28 resulting in fixation of the cannula 10 against push in and pull out. With respect to the embodiment shown in FIGS. 1-3, varying amounts of nested helixes 16 can be used. For structural integrity, it is preferred that at least two nested helixes 16 be used. However, additional amounts can be used without departing from the spirit of the invention.

The sleeve 12 can be made from the same materials as the cannula. Preferably, a thermoplastic can be used. As an alternative method of fixating the knob 26, the cannula 10 can have a series of circumferential ridges or portions thereof. The ridges facilitate longitudinal fixation. Fixation against rotation by knob 26 can be accomplished by interference of parts of longitudinal ridges on cannula 10 which engage knob 26 to resist rotation tending to collapse the helixes 16.

The position of cannula 10 can be adjusted by reversing the direction of rotation on knob 26 thereby relaxing the helixes 16 to the position shown in FIG. 1.

The sleeve can be a solid flexible member that can deform under a given load to expand above and below the opening 28. The force can be mechanical, pneumatic, or liquid.

Figure 4:
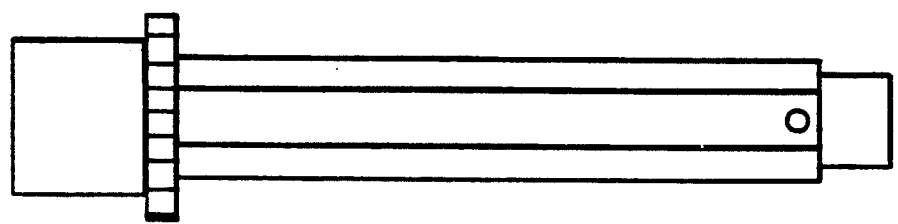
FIG. 4 shows the cannula with longitudinal strips in the contracted position.

Another embodiment of the invention, as shown in FIG. 4, utilizes longitudinally extending rather than spiral strips. The operation of this device is similar to that of cannula 10 and sleeve 12 although radial expansions of the sleeve occur by moving its ends together.

The foregoing disclosure and description of the invention are illustrative and explanatory thereof, and various changes in the size, shape and materials, as well as in the details of the illustrated construction, may be made without departing from the spirit of the invention.

I claim:

1. A fixation apparatus to hold an object to an opening in a body wall comprising:
   a flexible elongated member having a proximal and distal end expanding outwardly under a force when confronted with low or no resistance while being held against substantial expansion when contacting the body wall opening, whereupon the object is secured as said member expands further on either side of the opening than at the opening, said expansion on either side of said opening self-adjusting to the wall thickness by virtue of the wall holding the portion of said member adjacent said wall from substantial expansion.

2. The apparatus of claim 1, wherein said elongated member expands outwardly against low or no resistance when subjected to a compressive force.

3. The apparatus of claim 1, wherein said elongated member expands outwardly against low or no resistance when subjected to a torsional force.

4. The apparatus of claim 1, wherein said elongated member is formed having at least one longitudinal cut extending along the length thereof said cut facilitating outward expansion of said member.

5. The apparatus of claim 4, wherein said cut spirals around said member as said cut extends along the length thereof.

6. The apparatus of claim 5, further comprising:
   fixation means for attaching said member to the object to facilitate transmitting a force thereto;
   latch means on said member to selectively retain said member in an outwardly expanded position; and
   grip means associated with said member to facilitate application of force to said member.

7. An apparatus for securing an object to an opening in a body wall comprising:
   a singular expanding member at said opening mounted to the object for simultaneously securing the object against forcibly being easily pushed in and pulled out at said opening.

8. The apparatus of claim 7, wherein said expanding member is responsive to a force applied thereto to expand, with the opening providing resistance to expansion, whereupon said member expands further on either side of said opening to secure the object.

9. The apparatus of claim 8 wherein said expanding member further comprises:
   an elongated member having a proximal and distal end, said elongated member formed from a flexible material that expands outwardly under a force against low or no resistance while substantially retaining its shape under resistance offered by the opening in the body.

10. The apparatus of claim 9, wherein said elongated member expands outwardly against low or no resistance when subjected to a compressive force.

11. The apparatus of claim 9, wherein said elongated member expands outwardly against low or no resistance when subjected to a torsional force.

12. The apparatus of claim 9, wherein said elongated member is tubular and has at least one longitudinal cut extending along the length thereof, said cut facilitating outward expansion of said member.

13. The apparatus of claim 12, wherein said cut spirals around said member as said cut extends along the length thereof.

14. The apparatus of claim 12, wherein there are at least two cuts and each said cut is parallel to the longitudinal axis of said elongated member.

15. The apparatus of claim 13, further comprising:
fixation means for attaching said member to the object to facilitate transmitting a force thereto;
latch means on said member to selectively retain said member in an outwardly expanded position; and
grip means associated with said member to facilitate application of force to said member.

16. A method of securing an object to a body opening comprising the steps of:
providing a securing member and attaching it to the object, the securing member having a flexible, longitudinally extending body;
inserting the object into the opening so that a portion of the securing member extends on each side of the body opening;
applying a force to the securing member mounted to the object in order to radially expand the securing member, whereby the securing member will expand simultaneously on either side of the opening to a size bigger than said opening to secure the object, the securing member being substantially retained against radial expansion by said opening.

17. The method of claim 16, wherein said flexing step further comprises:
forcing at least one elongated member formed by at least one pair of cuts to outwardly expand where low or no resistance is offered; and
using the body opening to overcome the tendency of a portion of the elongated member to outwardly expand beyond the size of the opening.

18. The method of claim 17, further comprising:
moving at least one of the ends of said elongated member toward the other end to thereby expand a portion of said elongated member, intermediate to the ends thereof, radially outwardly.

19. The method of claim 18, further comprising:
rotating at least one end of said elongated member relative to its opposite end to expand at least a portion of said member.

20. The method of claim 19, wherein said forcing step further comprises:
twisting at least one end of the elongated member, which is formed by virtue of spiral cuts;
expanding the alongated member further on either side of the body wall than at the opening.

21. The method of claim 20, further comprising:
selectively retaining the expanded position of the elongated member to prevent release of the object.

22. The method of claim 21, wherein said applying a forcing step further comprises:
pushing a portion of the proximal end of the fixation member.

23. The method of claim 22, wherein said applying a forcing step further comprises:
turning said portion while pushing it.

* * * * *